US006410509B1

(12) United States Patent
Triebel (10) Patent No.: US 6,410,509 B1
(45) Date of Patent: Jun. 25, 2002

(54) USE OF MHC CLASS II LIGANDS AS ADJUVANT FOR VACCINATION AND OF LAG-3 IN CANCER TREATMENT

(75) Inventor: Frederic Triebel, Versailles (FR)

(73) Assignees: Institut Gustave-Roussy, Villejuif Cedex (FR); Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/492,113

(22) Filed: Jan. 27, 2000

Related U.S. Application Data

(63) Continuation of application No. PCT/EP98/04621, filed on Jul. 23, 1998.

(30) Foreign Application Priority Data

Jul. 25, 1997  (EP) .............................................. 97401800

(51) Int. Cl.[7] ........................ A61M 36/14; A61K 38/19; C07K 14/47; C07K 14/52

(52) U.S. Cl. .............................. 514/2; 514/21; 424/111; 424/184.1; 424/184.5; 424/193.1; 424/278.1; 530/350; 530/351

(58) Field of Search ..................... 514/2, 21; 424/184.1, 424/185.1, 193.1, 1.11, 278.1, 184.5; 530/350, 351

(56) References Cited

FOREIGN PATENT DOCUMENTS

| EP | 0 385 909 | 9/1990 |
|----|-----------|--------|
| EP | 0 394 827 | 10/1990 |
| WO | 89 02922 | 4/1989 |
| WO | 90 01870 | 3/1990 |
| WO | 91 10682 | 7/1991 |
| WO | 95 21528 | 8/1995 |
| WO | 95 30750 | 11/1995 |
| WO | 96 04386 | 2/1996 |
| WO | 96 17874 | 6/1996 |
| WO | 96 20215 | 7/1996 |
| WO | 97 24132 | 7/1997 |

OTHER PUBLICATIONS

Faure et al, "Soluble polypeptide fractions of the LAG-3 protein", NCBI, PubMed Database, Accession No. AAE27624, Aug. 2000.*

Lazar et al, "Transforming Growth Factor Alpha: Mutation of Aspartic Acid 47 and Leuine 48 Results in Different Biological Activities", Molecular and Cellular Biology, vol. 8, pp. 1247–1252, 1988.*

Burgess et al "Possible Dissociation of the Heparin–binding and Mitogenic Acitivies of Heparin–binding Growth Factor–1 from Its Receptor–binding Activities by Site–directed Mutagenesis of a single Lysine Residue", Journal of Cellular biology, vol. 111, pp, 1990.*

Kang et al, "Immunization with Soluble CD4–gp 120 complex Preferentially Induces Neutralizing Anti–human Immunodeficiency Virus type I Antibodies. . . ", Journal of Virology, vol. 68, No. 9, pp. 5854–5862, Sep. 1994.*

Pelikan et al, "Autoimmune mechanisms in the pathogenesis of neurologic paraneoplastic diseases" (Abstract only), Bratislavske Lekarske Listy, vol. 98, No. 6, pp. 335–338, Jun. 1997.*

Abbas et al. Cellular and Molecular Immunology, pp. 153–155, 1991.*

Takebe et al., "SRα Promoter: an Efficient and Versatile Mammalian cDNA Expression System Composed of the Simian Virus 40 Early Promoter and R–U5 Segment of Human T–cell Leukemia Virus Type 1 Long Terminal Repeat", *Molecular and Cellular Biology*, vol. 8, No. 1, pp. 466–472, (1988).

Chen et al., "Costimulation of Antitumor Immunity by the B7 Counterreceptor for the T Lymphocyte Molecules CD28 and CTLA–4", *Cell*, vol. 71, pp. 1093–1102, (1992).

Angevin et al., "Analysis of T–cell Immune Response in Renal Cell Carcinoma: Polarization to Type 1–Like Differentiation Pattern, Clonal T–cell Expansion and Tumor–Specific Cytotoxicuty", *Int. J. Cancer*, vol. 72, pp. 431–440, (1997).

Miyazaki et al., "Independent Modes of Natural Killing Distinguished in Mice Lacking Lag3", *Science*, vol. 272, pp. 405–408, (1996).

Huard et al., "T cell major histocompatibility complex class II molecules down–regulate CD4+ T cell clone responses following LAG–3 binding", *Eur. J. Immunol.*, vol. 26, pp. 1180–1186, (1996).

Huard et al., "Lymphocyte–activation gene 3/major histocompatibilty complex class II interaction modulates the antigenic response of CD4+ T lymphocytes", *Eur. J. Immunol.*, vol. 24, pp. 3216–3221, (1994).

Huard et al., "Characterization of the major histocompatibility complex class II binding site on LAG–3 protein", *Proc. Natl. Acad. Sci*, vol. 94 pp. 5744–5749, (1997).

Huard et al., "Cellular expression and tissue distribution of the human LAG–3–encoded protein, and MHC class II ligand", *Immunogentics*, vol. 39, pp. 213–217, (1994).

(List continued on next page.)

Primary Examiner—Anthony C. Caputa
Assistant Examiner—Karen A. Canella
(74) Attorney, Agent, or Firm—Browdy and Neimark (57) ABSTRACT

The present invention concerns the use of a MHC class II ligand, LAG-3, for the manufacture of a medicament for preventing or treating pathological conditions involving an antigen specific immune response, as well as the use of LAG-3 in cancer immunotherapy. The invention also concerns a pharmaceutical composition comprising an effective amount of an antigen together with an effective amount of human LAG-3, wherein LAG-3 s present as an adjuvant.

22 Claims, 8 Drawing Sheets

OTHER PUBLICATIONS

Triebel et al., "LAG–3 a Novel Lymphocyte Activation Gene Closely Related to CD4", *J. Exp.Med.*, vol. 171, pp 1393–1405, (1990).

Huard et al., "T cell MHC Class II Molecules Downregulated T Cell Proliferation following LAG–3 Binding", *Eur. J. Immunol.*, vol. 25, pp. 2718–2721, (1995).

Baixeras et al., "Characterization of the Lymphocyte Activation Gene 3–Encoded Protein. A New Ligand for Humand Leukocyte Antigen Class II Antigens", *J. Exp. Med*, vol. 176, pp. 327–337, (1992).

Wahren, "Gene Vaccines", *Immunotechnology*, vol. 2, pp. 77–83, (1996).

Dranoff et al., "Prospects for the Immunotherapy of Cancer Using Genetically Modified Tumors Cells", *Klinische Pharmakologie*, vol. 9, pp. 22–29, (1992).

Williams et al., "Genetic Infection Induces Protective In Vivo Immune Responses", *DNA and Cell Biology*, vol. 12, No.8, pp. 675–683, (1993).

Huard et al., "Cellular expression and tissue distribution of the Human LAG–3–encoded protein, an MHC Class II ligand", *Immunogenetics*, vol. 39, pp. 213–217, (1994).

Huard et al., CD4/major histocompatibility complex class II interaction analyzed with CD4–and lymphocyte activation gene–3 (LAG–3)–Ig fusion proteins, *Eur. J. Immunol.*, vol. 25, pp. 2718–2721, (1995).

McKinney et al., "A simple, non–chromatographic procedure to purify immunoglobulins from serum and ascites fluid", *Journal of Immunological Methods*, vol. 96 pp. 271–278, (1987).

Tighe et al., "Gene vaccination: plasmid DNA is more than just a blueprint", *Immunology Today*, vol. 19, No. 2, pp. 89–97, (1998).

Brunoquel et al., "Genomic Organization of the Human LAG–3/CD4 locus", *Immunogenetics*, vol. 47, pp. 96–98, (1997).

Koch et al., "High Level IL–12 Production by Murine Dendritic Cells: Upregulation via MHC Class II and CD40 Molecules and Downregulation by IL–4 and IL–10", *J.Exp. Med.*, vol. 184, pp. 741–746, (1996).

Wade et al. "Structural compartmentalization of MHC class II signaling function", *Immunology Today*, vol. 14, No. 11, pp. 539–546, (1993).

Pardoll et al., "Paracrine Cytokine Adjuvants in Cancer Immunotherapy", *Annu. Rev. Immunol.*, vol. 13, pp. 399–415, (1995).

Restifo et al., "Biology of Cellular Immune Response", *Biological Therapy of Cancer*, pp. 3–37, (1995).

Cosgrove et al., "Mice Lacking MHC Class II Molecules", *Cell*, vol. 66, pp. 1051–1066, (1991).

\* cited by examiner

USE OF MHC CLASS II LIGANDS AS ADJUVANT FOR VACCINATION AND OF LAG-3 IN CANCER TREATMENT

The present application is a continuation of International Application No. PCT/EP98/04621, filed Jul. 23, 1998, the priority of which is claimed persuant to 35 USC 120.

The present invention relates to the use of LAG-3 and CD4, and in a more general way, the use of MHC class II ligands or MHC class II-like ligands as adjuvants for vaccines, in order to boost an antigen specific immune response, as well as the use of LAG-3 as a therapeutical agent in cancer immunotherapy.

It is now recognized that the proteins encoded by MHC Class II region are involved in many aspects of immune recognition, including the interaction between different lymphoid cells such as lymphocytes and antigen presenting cells. Different observations have also shown that other mechanisms which do not take place via CD4 participate in the effector function of T helper lymphocytes.

The lymphocyte activation gene 3 (LAG-3) expressed in human $CD4^+$ and $CD8^+$ activated T-cells as well as in activated NK cells encodes a 503 amino-acids (aa) type I membrane protein with four extracellular immunoglobulin superfamily (IgSF) domains (1) and is a ligand for MHC class II molecules (2). Analysis of this sequence revealed notable patches of identity with stretches of aminoacids sequences found at the corresponding positions in CD4, although the overall aminoacids sequence homology with human CD4 is barely above background level (approximately 20% sequence identity). There are also some internal sequence homologies in the LAG-3 molecule between domains 1 (D1) and 3 (D3) as well as between domains 2 (D2) and 4 (D4) suggesting that LAG-3 has evolved like CD4 by gene duplication from a preexisting 2 IgSF structure (1). In addition, LAG-3 and CD4 genes are located in a very close proximity on the distal part of the short arm of chromosome 12 (3). LAG-3 and CD4 can therefore be regarded as evolutionary "first cousins" within the IgSF (2).

Like CD4, hLAG-3 is composed of lg like ectodomains with a WxC signature motif in domains 2 and 4; however a difference with CD4 is the presence of an extraloop sequence in domain 1 (recognized by the 17B4mAb) 30 and an intracytoplasmic proline rich motif (EP repeats) in human LAG-3 (hLAG-3). Recently, murine lymphocyte activation gene 3 (mLAG-3) was cloned and approximately 70% of homology was found with hLAG-3, with the same proline rich motif in the intracytoplasmic tail.

Antigen specific stimulation of $CD4^+$ T-cell clones in the presence of anti-LAG-3 mAb leads to extended proliferation and cytokines production (5). It has been suggested a regulatory role of hLAG-3 on $CD4^+$ T lymphocyte activated, by cross-linking MHC class II molecules expressed on T-cells with LAG-3 lg fusion proteins (6). LAG-3 MHC class II interaction inhibits signals through MHC class II molecules expressed on $CD4^+$ T-cells (decrease of proliferation and cytokines production), suggesting that both LAG-3 and MHC class II are effector molecules for the down-regulation of T helper cell mediated immune responses. The hLAG-3 lg fusion protein was found to bind xenogenic MHC class II molecules (murine and monkey). In addition, the mLAG-3 has been proposed to transduce a positive signal in effector cells, since transgenic mice with a LAG-3 null mutation have a defect in the NK cell compartment (7).

Mouse tumor cell lines engineered to express membrane (B7.1, B7.2. CD95L, . . .) or secreted molecules (IL-2, IL-12, . . .) are often used to investigate immune responses or antitumor effects. This approach implies that many tumor cells are potentially antigenic (9), and become immunogenic when they express molecules. Experimental mouse tumors are classified as intrinsically immunogenic when, after a single injection into syngenic mice as nonreplicating cell vaccines, they elicit a protective immune response against a subsequent lethal challenge. Tumors that do not retain this residual immunogenicity are defined as poorly immunogenic or nonimmunogenic.

Antitumor immune responses are mediated primarily by T-cells (12). Recent studies have implicated a deficit in efficient antigen presentation and T-cell priming as being problematic for the practical implementation of an ideal tumor vaccine. Indeed, it has been demonstrated that transfecting tumor cells with genes coding for various cytokines, such as IL-2, IL-4, IL-12 or GM-CSF or genes coding for co-stimulatory molecules such as B7 not only led to primary rejection of the modified cells but often elicited protective immunity against subsequent challenge with unmodified tumor cells (13).

Professional antigen presenting cells (APCs) are capable of taking up, processing and presenting antigen to T-cells in the context of co-stimulatory signals required for T-cell activation, leading to optimal antigen presentation. In particular, it is well established that MHC class $II^+$ dendritic cells (DCs) play a crucial role in processing and presenting antigens to the immune system. The inventors hypothesized that tumor immunogenicity would be increased if tumor could be modified to directly trigger host APCs such as macrophages and dendritic cells. Indeed, it has been reported that cross-linking of MHC class II molecules specifically expressed by such cells, using mAb or superantigens, transduces signals resulting in $TNF\alpha$ and IL-12 production (14, 15). They had previously reported that Lymphocyte Activation Gene-3 (LAG-3), which is embedded in the CD4 locus (1, 16), encodes a protein that binds human and murine MHC class II molecules with higher affinities than CD4 (17, 6).

The inventors of the instant application have investigated whether hLAG-3, human CD4 (hCD4) and mLAG-3 expression on three MHC class II-mouse tumors (the poorly immunogenic sarcoma MCA 205 and the nonimmunogenic TSIA+RENCA adenocarcinoma) can mediate an immune response so as to reject mouse tumor and can induce systemic immunity.

As a result, they have discovered that human or murine LAG-3, whether expressed as membrane proteins in solid tumor cell lines or inoculated into mice as a soluble protein induced a potent immunity against highly malignant murine tumors. The immunity was T-cell dependent and antigen-specific.

They have further investigated the role of CD4 and found that human CD4 (hCD4) also induced a systemic antitumor response.

The induced immunity has been found to be T-cell mediated, since the same antitumor response was obtained with Nude mice lacking T-lymphocytes.

The antitumor effect was still found when using different tumor cell lines exhibiting different intrinsic immunogenicity as well as different strains of mice expressing different MHC genes.

Furthermore, the hLAG-3 and hCD4 induced effects were observed when tumor cell lines expressing hLAG-3 or hCD4 were injected at a distant site from the initial inoculation site of the wild-type tumor cell lines.

Furthermore, systemic administration of soluble hLAG-3 directly induces an inhibition of in vivo tumor growth.

All the aforementioned results demonstrate that LAG-3 and CD4 are able to elicit an antigen specific T-cell mediated immune response and may be useful as a tool in immunotherapy, in order to prevent the occurrence of a cancer among populations at risk or more generally in any immunotherapy involving an antigen-specific T-cell mediated immune response, and that LAG-3 is further useful as a tool for inhibiting in vivo tumor growth.

The inventors have further demonstrated that soluble LAG-3 when administered together with an antigen against which an immune response is sought, was able to work as an adjuvant for a vaccine.

This role can be explained by an improved presentation of the antigen by professional APCs (dendritic cells and macrophages) located underneath the skin and triggered via MHC class II.

Accordingly, since induction of a $CD8^+$ T-cell immunity is involved in viral (e.g. AIDS, hepatitis and herpes) and intra-cellular parasitic and bacterial (e.g. leprosy tuberculosis) infections and cancer, LAG-3 will be particularly useful for therapeutic vaccination against the pathogen agents involved in these diseases as well as in cancer treatment.

According to one of its aspects, the present invention relates to the use of a MHC class II ligand or a MHC class II-like ligand for the manufacture of a medicament for preventing or treating pathological conditions involving an antigen specific immune response, preferably an antigen-specific T-cell mediated immune response.

In a first embodiment, the MHC class II binding molecule is LAG-3 as well as derivatives thereof, able to bind HC class ligand of LAG-3.

By derivatives of LAG-3, in the sense of the present invention, there are meant mutants, variants and fragments of LAG-3 namely soluble fragments of LAG-3 provided that they maintain the ability of LAG-3 to bind MHC class II molecules.

Thus, the following forms of LAG-3 may be used:
the whole LAG-3 protein,
a soluble polypeptide fragment thereof consisting of at least one of the four immunoglobulin extracellular domains, namely the soluble part of LAG-3 comprised of the extracellular region stretching from the aminoacid 23 to the aminoacid 448 of the LAG-3 sequence disclosed in French Patent application FR 90 00 126,
a fragment of LAG-3 consisting of substantially all of the first and second domains
a fragment of LAG-3 consisting of substantially all of the first is and second domains or all of the four domains, such as defined in WO 95/30750, such as
a mutant form of soluble LAG-3 or a fragment thereof comprising the D1 and D2 extracellular domains and consisting of:
a substitution of an aminoacid at one of the following positions:
position 73 where ARG is substituted with GLU,
position 75 where ARG is substituted with ALA or GLU,
position 76 where ARG is substituted with GLU, or a combination of two or more of those substitutions,
a substitution of an aminoacid at one of the following positions:
position 30 where ASP is substituted with ALA;
position 56 where HIS is substituted with ALA;
position 77 where TYR is substituted with PHE;
position 88 where ARG is substituted with ALA;
position 103 where ARG is substituted with ALA;
position 109 where ASP is substituted with GLU
position 115 where ARG is substituted with ALA;
or a deletion of the region comprised between the position 54 and the position 66,
or a combination of two or more of those substitutions.
Those mutants are described in PNAS, June 1997 (4)
or a physiological variant of LAG-3 comprised of a soluble 52 kD protein containing D1, D2 and D3.

According to a second embodiment, the MHC class II binding protein is CD4 or a derivative thereof able to bind the MHC class II ligand of CD4.

The derivatives of CD4 are such as defined for the derivatives of LAG-3. They are namely mutants, variants and fragments of CD4 namely soluble fragments of CD4 provided that they maintain the ability of CD4 to bind MHC class II molecules.

LAG-3 and CD4, namely hLAG-3 and hCD4 or the derivatives thereof such as defined above may be administered as recombinant moieties expressing said molecules, for example transfected cells or recombinant viruses.

The present invention relates also to tumor cells transfected with a DNA coding for at least one MHC class II ligand, such as CD4 or LAG-3 or derivatives thereof.

A further object of the instant invention is also the use of cells, like tumor cells, transfected with a DNA coding for at least one MHC class II ligand, such as CD4 or LAG-3 or derivatives thereof for the manufacture of a medicament, preferably a medicament for preventing or treating pathological conditions involving an antigen specific immune response like an antigen specific T-cell mediated immune response or for treating pathological disorder like cancers.

The transfected cells are preferably mammal cells and in particular mammal tumor cells.

According to one of its aspects, the present invention relates to a process for preparing cells transfected with a DNA coding for at least one MHC class II ligand, such as CD4 or LAG-3 or derivatives thereof comprising the steps consisting of removing cells from a patient, transfecting said cells with a DNA coding for at least one MHC class II-like ligand, such as CD4 or LAG-3 or derivatives thereof and recovering the so-transfected cells.

For the preparation of tumor cells according to the invention, this process will be reproduced on tumor cells removed from a patient.

However, according to a preferred embodiment, the MHC class II binding protein, namely CD4 or LAG-3 or the derivative thereof, is administered in a free form, namely in a soluble form by inoculating them systemically, for example as an s.c, i.m or i.v injection.

The medicament according to the invention may be used as a vaccine to prevent disorders associated with an antigen specific immune response, preferably a T-cell mediated immune response.

To that end, it is administered in a suitable vehicle together with one or several antigen(s) against which an immune response is sought. The antigen may be an inactivated or attenuated infectious agent or a purified antigen, eventually obtained by protein recombinant procedures, such as an antigen of an infectious agent or a tumor antigen, which preferably are able to elicit a T-cell mediated immune response.

The vaccine may be used to prevent a subject against an infectious disease, such as a viral, bacterial or parasitic disease wherein the infectious agent elicits an antigen specific immune response, preferably a T-cell mediated immune response.

The vaccine may also be used for treating patient against an infectious disease such as mentioned hereabove, involving a T-cell mediated immune response, namely a CD8+ T-cell mediated immune response.

Examples of diseases requiring a boost of an existing T-cell mediated immunity are provided in the following table.

TABLE

| Pathogens | Agents | Diseases |
|---|---|---|
| Viruses | HIV | AIDS |
| | HBV, HCV | Hepatitis |
| | HSV, CMV, HHV | Failure of transplantation, Kaposi sarcoma |
| | HTLV1 | Cancer |
| Intra-cellular Bacteria | Listeria | Listeriosis |
| | Mycobacteria | Leprosis, Tuberculosis |
| Intra-cellular Parasites | Plasmodium Etc | Malaria |
| | Oncogenes Etc | Most carcinomas, melanomas, leukemia |

In such cases, the antigen is chopped in the cells and the corresponding peptides loaded into MHC class I molecules and presented at the surface of the cells where there are recognized by CD8+ cells. The results of the inventors showing that LAG-3Ig molecules induce efficient T-cell response in animals and stimulate immature dendritic and monocytes in vitro strongly suggest that LAG-3 is a natural T-cell adjuvant in situations where it can cross-link MHC class II molecules in professional APCs.

The vaccine may also be used to prevent a subject against cancer, either solid tumor cancer or leukemia.

The vaccine may further be used for treating a patient against cancer.

In that case, the MHC class II binding protein namely LAG-3 or CD4 is administered to a subject either subcutaneously, intradermically or as a nasal spray together with one or several antigens able to elicit an immune response, preferably a T-cell mediated immune response. The antigen may be a peptide, a lipopeptide, a recombinant protein or DNA coding for these antigens.

The anti-cancer vaccine may be inoculated to populations at risks identified by their genotype (preventive vaccine) or to patients (therapeutic vaccine) bearing a tumor or at high risk of relapse following surgery.

Whether the vaccine is used as a conventional vaccine (preventive) or a therapeutic vaccine, it may be administered as a "naked" plasmid (19) incorporating a DNA sequence encoding LAG-3 or CD4, preferably under the control of a strong promoter.

The plasmid preferably also contains DNA encoding the antigen against which an immune response is sought.

A further object of the instant invention is thus a pharmaceutical composition comprising an effective amount of a MHC class It ligand in combination with an effective amount of an antigen able to stimulate the immune system, preferably via a T-cell response.

In still another aspect, the present invention relates to the use of LAG-3 as a medicament for anti-cancer immunotherapy in patients bearing a cancerous tumor.

In that case, LAG-3 is administered preferably as a free LAG-3 protein or a derivative thereof in a pharmaceutically acceptable vehicle, preferably a soluble derivative such as defined previously.

LAG-3 may be administered as an intratumoral injection or systemic injection, for example s.c, i.v or i.m.

A further object of the present invention relates to a method for tumor gene therapy comprising the steps consisting of removing a portion of a patient tumor cells, transfecting said cells with a DNA coding for at least one MHC class II ligand, such as CD4 or LAG-3 or derivatives thereof and re-introducing the so-transfected cells into the patient.

The following examples demonstrate the activity of LAG-3 and CD4 in the prevention or treatment of pathological conditions involving a T-cell mediated immune response.

For the better understanding of the invention, it may be referred to the annexed figures wherein.

the figure inside the frame of FIG. 6 represents the percentage of mice with tumor.

FACS analysis of CD8 expression by TILs from control (wt MCA 205) mice compared with TILs from hLAG-3 MCA 205 mice. b, CD8+ T-cells contributes to the control of hLAG-3 TS/A tumor growth. Mice received i.p. 200 µg of purified CD4 or CD8-specific mAb at day−3,−2,−1,+4 and+8. Wild type or hLAG-3 TS/A tumor cells (MTD) were inoculated s.c. at day 0. Data are means±s.e.m. of 5 mice in each group from a single experiment. These experiments were performed twice with similar results. c) Increased activity of antitumor CTLs in mice which had rejected hLAG-3/TS/A cells. Mice received transplants s.c. of $5 \times 10^4$ hLAG-3/TS/A cells and were rechallenged at day 30 with $2.5 \times 10^5$ parental TS/A cells. Spleens were collected at day 60 in tumor-free mice and the cells were co-cultured for 6 days with the indicated target cells that had been irradiated. Cytolytic activity against indicated target cells were examined in a standard 4 h $^{51}$Cr release assay with different effector-to-target ratios (E:T). Results for two mice are shown. These experiments were performed twice on 4 mice with similar results.

The experiments illustrated in the examples were carried out by using the following materials and methods.

MATERIALS AND METHODS

1 Tumor Cell Lines

The MHC Class I$^+$ and Class II$^-$ tumor cell lines used were the poorly immunogenic methylcholanthrene-induced sarcoma MCA 205 cell line, (syngenic from C57BL/6 H-2$^b$ mice), the immunogenic renal carcinoma cell-line RENCA and the non-immunogenic undifferentiated spontaneous mammary adenocarcinoma TS/A cell line (both syngencic from BALB/C H-2$^d$ mice). The MC38 colon carcinoma cell line (syngenic from C57BL/6 mice) was used in rechallenge experiment as control tumor. Cells were maintained at 37° C. in a humidified 10% $CO_2$ atmosphere in air, in complete medium (RPMI 1640 culture medium supplemented with glutamine, sodium pyruvate, penicillin/streptomycin, 10% of endotoxin free fetal calf serum and 0.05 mM 2-β mercapto-ethanol). For immunostaining experiments and in vivo experiments, cells were removed from their culture vessels with PBS containing 1 mM EDTA. Before subcutaneous injection (s.c), cells were washed three times in cold PBS 1X and resuspended in same buffer. Cells were not cultured for longer than two weeks.

2. Mice

Female C57BL/6 mice, 6 or 8 weeks old, were purchased from IFFRA-CREDO Laboratories (Lyon, France). Female BALB/c mice, 4 to 8 weeks old were purchased from JANVIER Laboratories, (France). All this mice strains were raised in specific pathogen free conditions. Female Nude were purchased from the animal facility of Institut Gustave Roussy and kept under protected microenvironments.

3. Genetic Constructs

The cDNAs of hLAG-3, mLAG-3 and hCD4 were cloned into NT hygromycin plasmid vector (cloning sites are Xbal for hLAG-3 and HCD4 and Xhol for mLAG-3, under SRoc promoter (18). The LAG-3 hcDNA cloned in a reverse orientation was used as a negative control. All tumor cell lines (2.5×10$^6$ cells) were transfected by electroporating using an Eurogentec apparatus (Belgium): MCA 205 cells at 200V, TS/A and RENCA cells at 300V, 1500 μF and infinite shunt resistance. Transfectants were selected in hygromycin B (Sigma): MCA 205 in 100 μg/ml RENCA and TS/A transfectants in 200 μg/ml. Resistant cells expressing the transfected molecules were identified using a Elite cytofluorimeter (Coulter, Hialeah, FL) and cloned by limiting dilution. The best clone for each construction in each tumor cell lines was used in this study.

4. Cytofluorimetric Analysis

Resistant cells expressing the transfected molecules were stained by indirect immunofluorescence, with saturating amounts of purified or ascites fluids mAbs. Cells were first incubated with mAbs : 17B4 (anti-hLAG-3.1) (2), OKT4 (anti-hCD4), a rabbit preimmunserum (termed PIS) used as negative control and a rabbit immunserum anti-mLAG-3 (termed IS). The expression of murine MHC class I and II molecules on tumors were detected with the following mAbs 34-1-2S for H-2 K$^d$ and D$^d$, 28-8-6S for H-2 K$^b$ and D$^{b,}$ 14-4-4S (for E$^d$), M50114 (for IA and IE).

Cells were then washed and incubated with FITC-conjugated goat anti-mouse serum (GAM Coulter) or FITC-conjugated goat anti-rabbit serum (GAR Southern Biotechnologies Inc.). To study presence of infiltrating cells or recruitement of cells in tumor periphery, some mice were killed and tumor dissociated. Cells were stained by direct immunofluorescence, with 17B4-FITC or the following mAbs (Pharmingen) anti-mCD4-PE (L3T4), anti-mCDB (Ly-2 and Ly-3.2), anti-mNK (2B4) and anti-mCD22 (Lyb-8.2). Cells were sorted using a Elite cytofluorimeter Coulter).

Positive cell lines were then cloned by limiting dilution LAG-3$^+$ or CD4$^+$ clones were frozen for further use.

To generate soluble LAG-3 molecules, the extracellular domains of hLAG-3 and mLAG-3 were fused to the higG1 and mIgG2a Fc portions respectively, as described (6). The resulting recombinant proteins, hLAG-3Ig and mLAG-3Ig, were produced in CHO cells and purified on protein-A columns.

5. In Vivo Tumor Experiments

5.1 Tumor Growth Establishment and Vaccination

Establishment of tumor cell lines was performed s.c using the minimal tumorigenic dose (MTD) at 2.10$^5$ cells/mouse for MCA 205, 5.10$^4$ cells for TS/A and 10$^5$ cells for RENCA or fivefold the MTD. Mice which were tumor free 30 days after injection were rechallenged with parental tumor cell line (5×MTD). MC38 colon carcinoma cell line was used at 10$^5$ cells as a control tumor in C57BL/6 mice that rejected TS/A tumor. Age-matched naive C57BL/6 or BALB/c mice were injected with tumor cell lines.

Tumor growth was monitored two to three times a week by measuring two perpendicular tumor diameters using calipers. At day in vivo tumor experiments, cells were analysed by cytofluorimeter and in vitro proliferation assay made.

5.2 Tumor Therapy Models

On day 0, wild-type tumor cell lines were inoculated s.c. in the left flank (MTD). On day 0, 3 or 6, LAG-3$^+$ tumor cells were injected into the right flank (MTD or fivefold MTD) to determine the antitumor effects on the nontransfected cells at a distant site. Tumor growth was monitored as described before.

5.3 For cytometric analysis, mice were inoculated s.c. with 5×MTD tumor cells as described above. Day 8 tumors were dissociated and analyzed with CD3-PE, CD4-PE, CD8-PE, CD80-FITC, CD86-FITC, 2B4-PE (NK-cell), CD22-PE (B-cell) or hLAG-3-FITC mAbs with an Elite cytofluorimeter (Coulter).

5.4 For lymphocyte depletion, mice received i.p. 200 μg of purified (18) anti-CD4 (YTS 191.1.2) or anti-CD8 (YTS 169.4.2.1) mAb at day−3,−2,−1,+4 and+8. Wild type or hLAG-3 TS/A tumor cells were inoculated s.c. at day 0 (MTD). Cytofluorimetric analysis of control mice receiving these doses of mAb showed more than 95% reduction of the target population in spleen (data not shown).

6. Studies in vitro

For cytotoxicity assays, tumor specific short term CTL were generated using mixed lymphocyte tumor cell culture. Briefly, 3×10$^7$ spleen cells were collected at day 30 from mice that had rejected established tumors. These cells were stimulated with 3×10$^6$ irradiated parental tumor cells in complete medium for 4 days and then supplemented with 50 IU/ml of recombinant hIL-2 (Cetus) for 2 days. The effector functions of splenocytes were tested at day 6 in a standard 4h $^{51}$Cr release assay (effector-to-target ratios from 25/1 to 200/1) against labelled target cells: autologous tumor cells, an H-$2^d$ irrelevant sarcoma WEHI 164 and a NK sensitive YAC cell line. The lysis percentage of triplicates was calculated as [(average experimental cpm−average spontaneous cpm)/(average maximum cpm−average spontaneous cpm)]×100. We user-defined specific lysis as lysis of mouse splenocytes that rejected tumor cells minus the lysis of naive mouse splenocytes.

RESULTS

EXAMPLE I

Surface Expression of hCD4, hLAG-3, mLAG-3 and MHC Molecules on Tumor Cell Lines.

Transfected tumor clones were stained as detailed in section 2.2, and analyzed to compare level expression of hCD4, hLAG-3 and mLAG-3. The best clone for each construct was used in this study. The following tumor cell lines TS/A express high levels of MHC class I molecules and MCA 205 express low levels of MHC class I. No significant difference was observed between MHC class I expression on parental tumor cell lines compared to transfected clones.

EXAMPLE II

Tumor Establishment Models and Vaccination:Comparative Effects of hCD4 and hLAG-3

Figure 1:
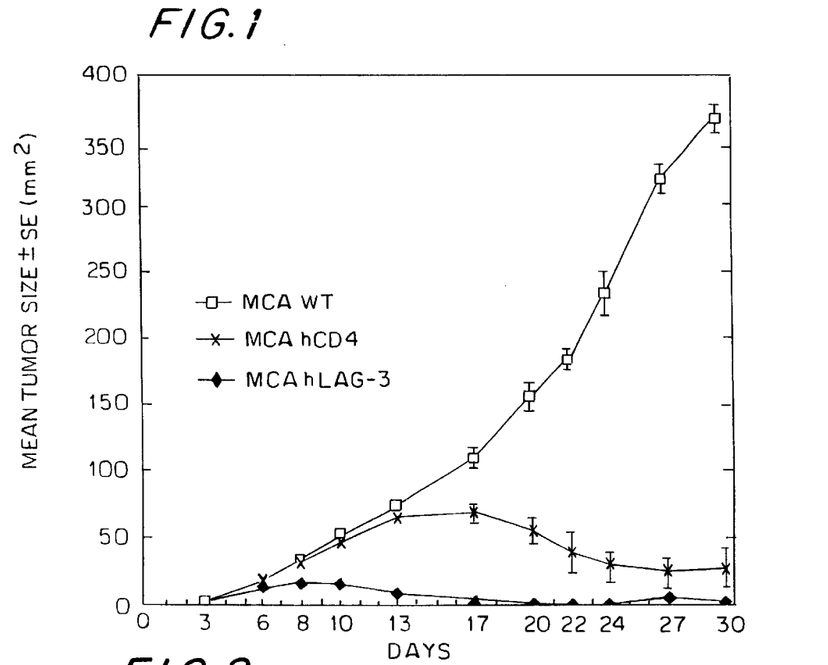
FIG. 1 represents the mean tumor size of C57BL/6 mice inoculated with wild-type MCA 205 tumor cells (MCA WT), MCA 205 tumor cells transfected with hCD4 (MCA hCD4) and MCA 205 tumor cells transfected with hLAG-3 (MCA hLAG-3)
Figure 4:
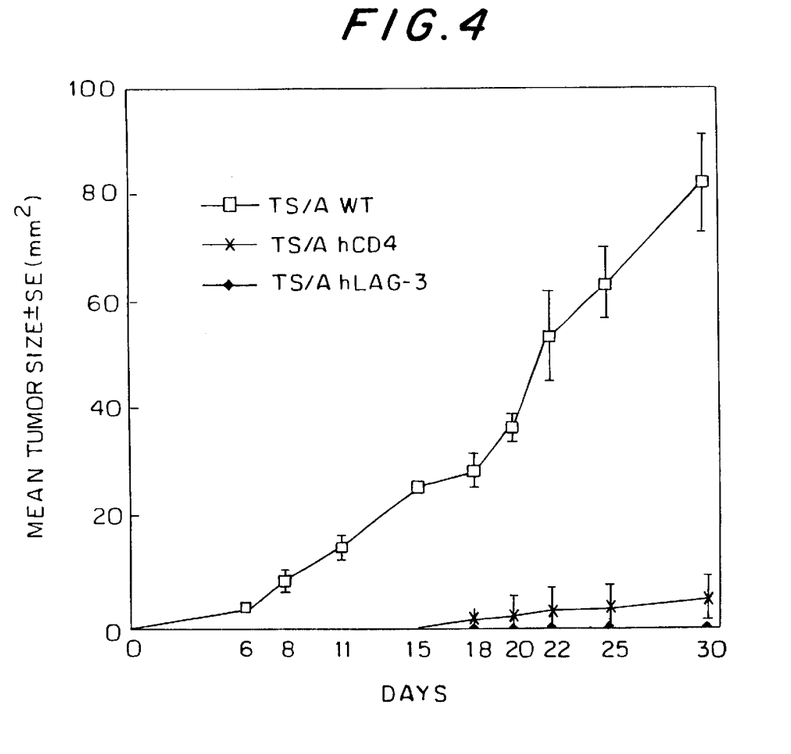
FIG. 4 represents the results (mean tumor size) obtained with a different strain of mice (BALB/c) and a different tumor cell line (TS/A) either of wild type (TS/A wt) or transfected with hCD4 (TS/A hCD4) or hLAG-3 (TS/A hLAG-3)

These experiments were performed to examine the tumorigenicity of cells after gene transfection: MCA 205 and TS/A as shown in FIGS. 1 and 4 and RENCA. The induction of antitumor immunity of LAG-$3^+$ tumor was compared to parental tumor cell lines.

Wild type MCA 205, TS/A and RENCA cells grew progressively when subcutaneously implanted into either syngeneic C57BL/6 or BALB/C mice or nu/nu mice. Tumor cells stably transfected following hydromycin selection with the hLAG-3 cDNA cloned in a reverse orientation had a similar growth rate.

Animals receiving MCA-LAG-3 rejected their tumor. Animals receiving MCA-CD4 exhibited a lower tumor growth than animals receiving wt MCA. Two of them (over 5) completely rejected the tumor (FIG. 1).

Similar results were obtained with mLAG-3 (data not shown).

These results indicate that ectopic expression of hLAG-3. mLAG-3 and hCD4 increases the immunogeniticy of MCA sarcoma cell line and prevents tumor formation of MCA transfectant, i.e. it induces a potent immunity against a highly malignant murine tumor.

Figure 2:
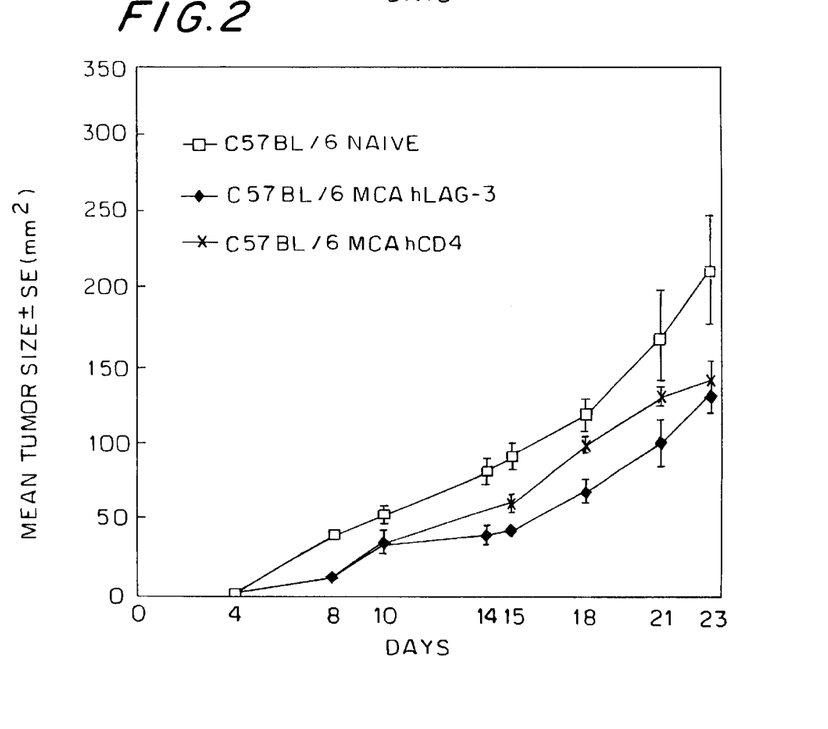
FIG. 2 represents the results (mean tumor size) obtained after rechallenging the same mice with wild-type MCA tumors cells at a minimal tumorigenic dose.

Similar results are obtained with TS/A tumor cells in BALB/c mice (FIG. 2).

Similar results are further obtained with RENCA tumor cells in syngeneic BALB/C mice.

Thus, antitumor effect is obtained:
in different strains of mice expressing different MHC complex genes;
using different tumor cell lines (exhibiting different intrinsic immunogenicity, TS/A<MCA).

Nude mice (nu/nu) were inoculated with wt MCA, MCA hLAG-3 and MCA hCD4 type tumor cells and transfectants grew similarly.

This substantiates the fact that systemic-, long-lasting-, tumor specific-hLAG-3 or hCD4- boosted immunity are T-cell mediated.

Mice previously inoculated with wt MCA, MCA hLAG-3 and MCA hCD4 and tumor free after 30 days injection with MTD were rechallenged (1 fold) with fivefold the MTD parental tumor cell line or with an unrelated syngeneic MC 38 colon carcinoma cell line.

Figure 3:
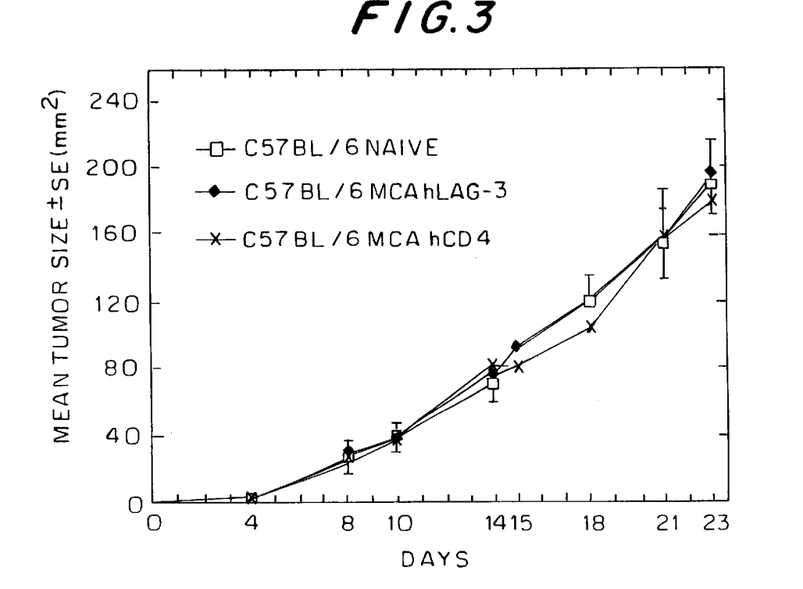
FIG. 3 represents the results (mean tumor size) obtained after rechallenging the same mice with the irrelevant MC 38 tumor cell line.

The results are represented in FIGS. 2 and 3.

After rechallenge, growth of wt MCA was delayed in surviving animals both for animals receiving MCA-LAG-3 cells and MCA-CD4 cells (FIG. 2).

No such effect was observed in animals rechallenged with irrelevant tumor MC38 (FIG. 3).

This indicates that both ectopic expression of hLAG-3 and hCD4 have an adjuvant-like effect and induces a long-lasting antigen specific immunity against the unmodified parental tumor.

EXAMPLE III

Therapy of wt MCA 205 Tumors in C57BL/6 Mice with MCA-hLAG-3

Three groups of five mice each were used for the experiment.

Each group was inoculated in one flank with wt MCA and three days later, with either MCA wt (group 1), MCA-hLAG-3 at $2.10^5$ cells (group 2) and MCA-hLAG-3 at $1.10^6$ cells (group 3).

Figure 5:
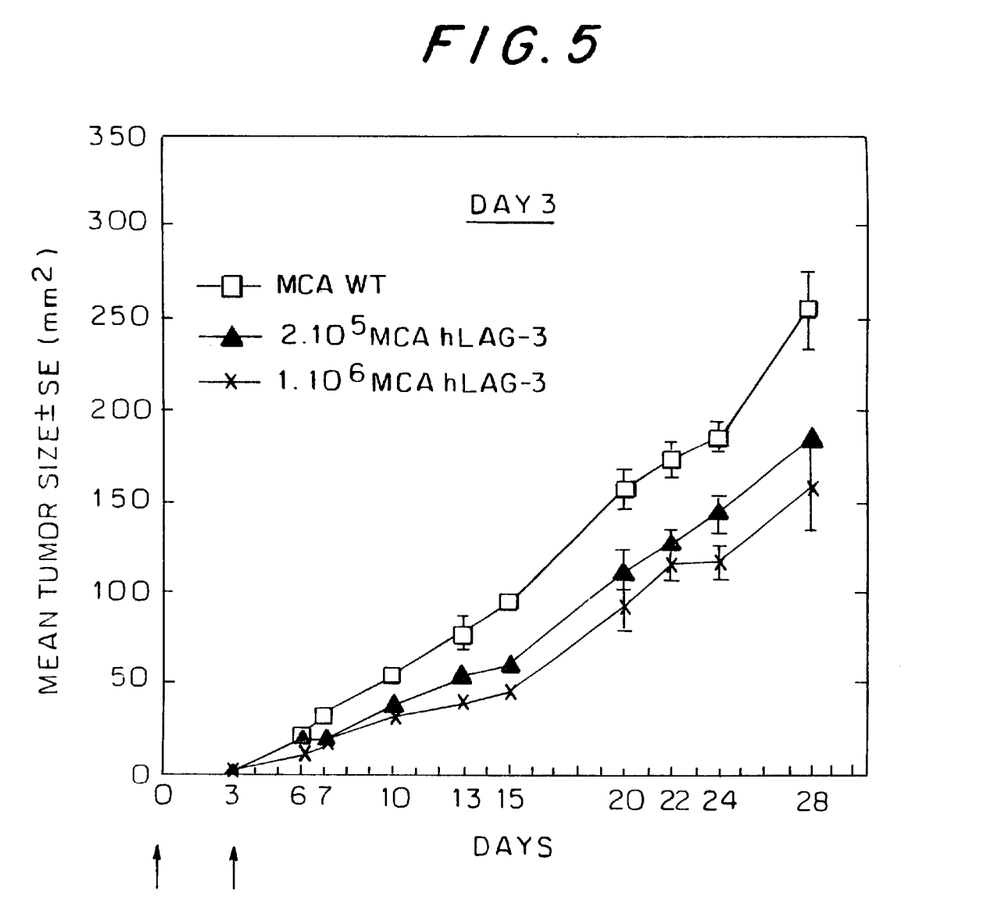
FIG. 5 represents the results (mean tumor size) obtained with existing tumors treated with different doses of MCA cells expressing hLAG-3.

The size of the original tumor was measured in each group over 30 days. The results are represented in FIG. 5.

Injection of MCA-hLAG-3 delayed the tumor growth in a dose dependent manner.

This experiment confirms the systemic effect of LAG-3 on tumor growth and indicate that LAG-3 represents a therapeutic agent against solid tumors.

EXAMPLE IV

Therapy of wt MCA 205 Tumors in C57BL/6 Mice with Soluble LAG-3

Three groups of five mice each were simultaneously inoculated with either wt MCA suspended in either PBS (group 1) or PBS containing soluble human LAG-3 (shLAG-3 D1 D4) in amounts of 25 $\mu$g (group 2) or 250 $\mu$g (group 3).

The size of the tumors were measured for each group over a period of 30 days.

Figure 6:
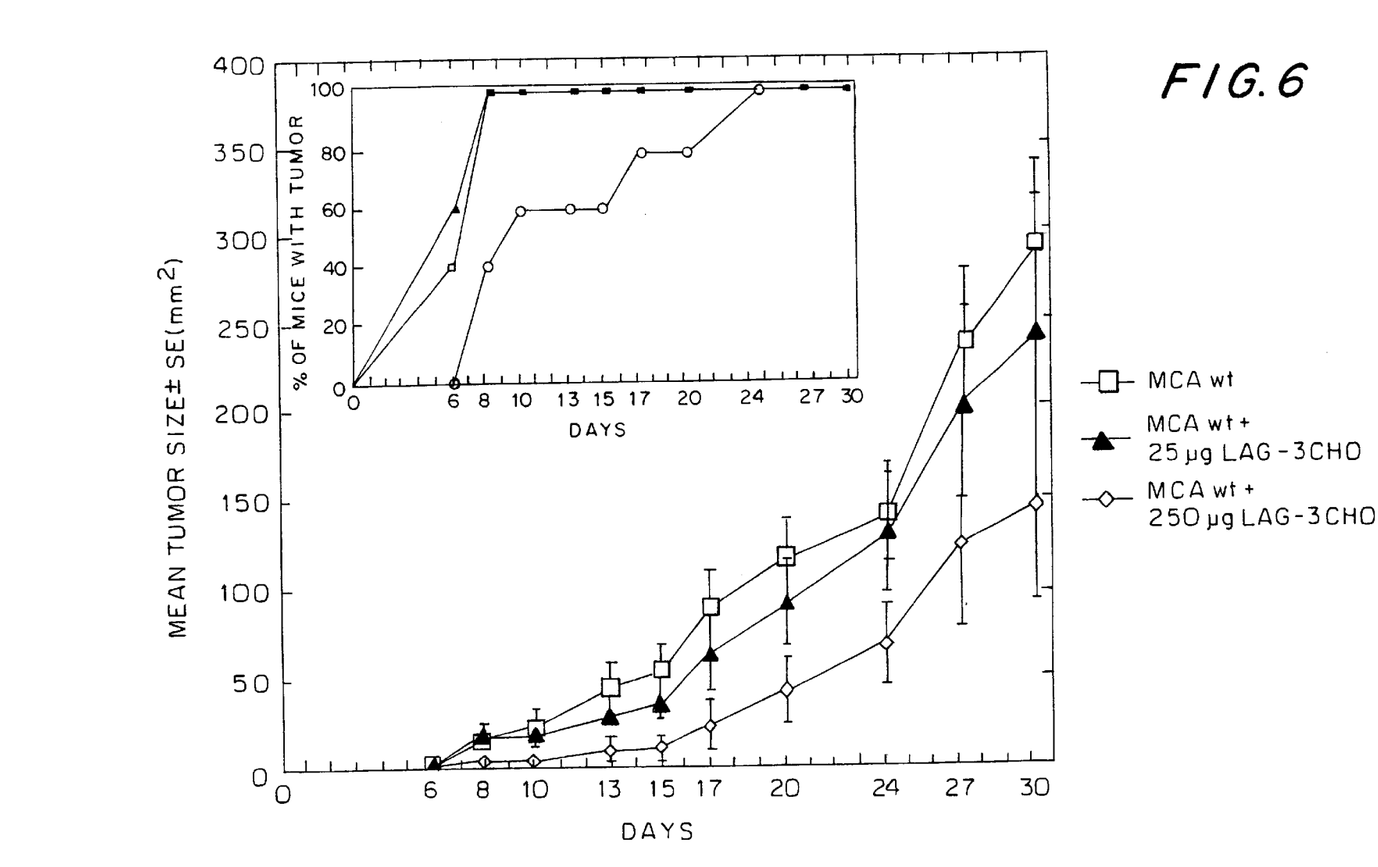
FIG. 6 represents the results (mean tumor size) obtained with soluble LAG-3 injected together with MCA cells (MCA wt, MCA wt+25 µg LAG-3 and MCA wt+250 µg LAG-3)

The results are represented in FIG. 6.

Co-administration of hLAG-3 D1 D4 induced a dose dependent tumor growth retardation.

This demonstrates that systemic administration of soluble hLAG-3 directly induces an inhibition of in vivo tumor growth.

EXAMPLE V

In Vivo LAG-3 Expression on Human Tumor Lymphocytes Infiltrating (TILs) Renal Cell Carcinoma (RCC)

In human, LAG-3 is expressed in tissues (i.e., inflammed secondary lymphoid organs) but not on the surface of PBMCs (3), even on in vivo-activated $CD25^+$, $CD69^+$ PBMCs. LAG-3 is expressed at higher levels on activated MHC class I-restricted $CD8^+$ cells than on MHC-class II-restricted $CD4^+$ cells (3) and LAG-3 expression induction by IL-12 or by the more potent combination IL-2 +IL-12 is stronger on $CD8^+$ than $CD4^+$ cells. LAG-3 is a weakly expressed activation antigen in vitro as well as in viva and it is sometimes difficult to assess the percentage and/or the specificity of fluorescence labelling in freshly dissociated tumors. Since LAG-3 may interfere with MHC class II$^+$ APCs in human tumors, we assessed its expression in a series of tumors known to be infiltrated by T-cells, using immunohistochemistry (the APAAP procedure). LAG-3 expression on TILs was detected in all samples tested, including 5 melanomas, 10 renal cell adenocarcinomas and 7 B-cell lymphomas.

Eight patients were investigated for LAG-3 expression on tumor infiltrating lymphocytes in renal cell carcinoma tumors.

Dissociated tumors were used for experiments by cytofluorometric assays. The expression of LAG-3 was studied among the lymphocyte population. determined by its size and granulosity. Dead cells were excluded from the study by staining with propidium iodide. TILs were positively stained with 17B4, a monoclonal antibody specific of the epitope of the extraloop of LAG-3.

Figure 7:
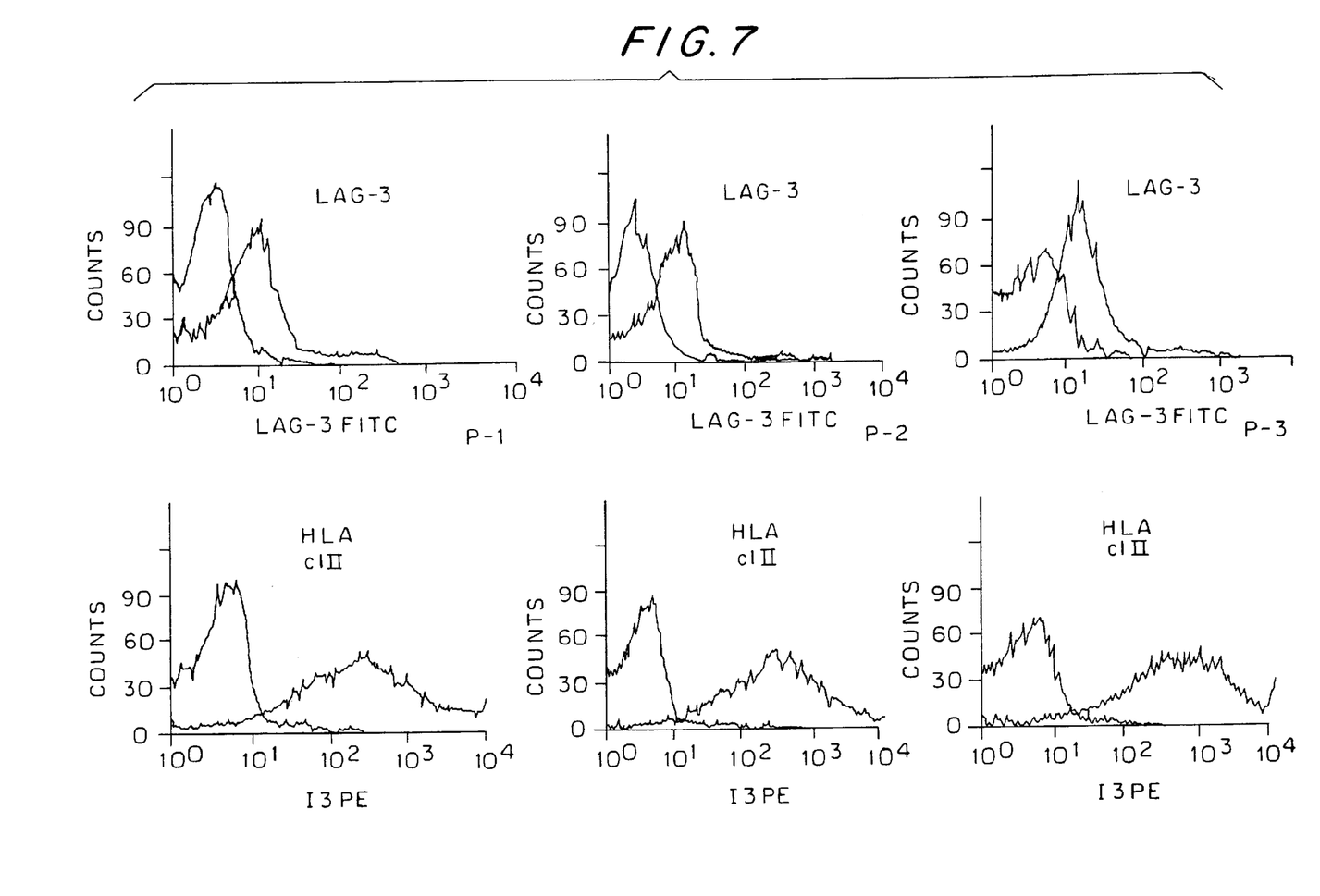
FIGS. 7 and 8 represent results of expression of LAG-3 in the membrane of tumor infiltrating lymphocytes (TILs) in five patients (P1–P5) bearing a renal cell carcinoma (RCC).
Figure 8:
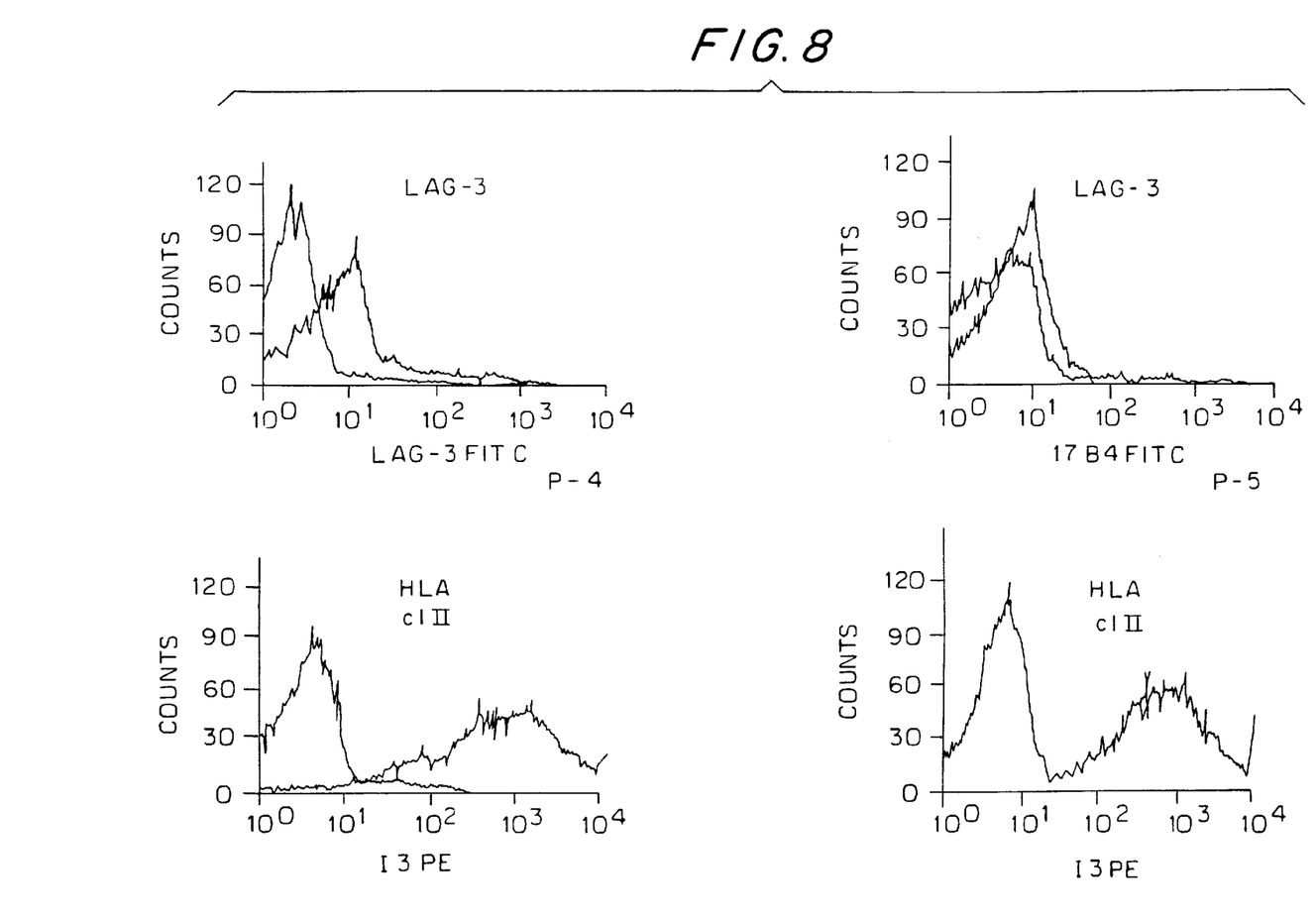

The results are represented in FIG. 7 for patients P1–P3 and FIG. 8 for patients P4 and P5.

For all patients, a shift of the fluorescent peak was observed showing the binding of the 17B4 antibody at the surface of the lymphocytes.

Thus, in all patients, TILs actually expressed LAG-3 with a significant percentage (30%) of RCC-TIL in unrelated patients.

In all samples CD3$^+$ T-cells were found to express LAG-3 (range 11%–48%) with higher expression on CD8$^+$ T-cells.

In contrast, peripheral blood mononuclear cells were LAG-3 in these patients, showing that LAG-3 expression on lymphocytes is a phenomenon related to T-cell activation in tumors.

Furthermore by using an ELISA assay, high concentrations (about 1 ng/ml) of soluble LAG-3 were found in blood of patients with cancer.

These data show that LAG-3 is a molecule involved in the naturally occurring antitumoral response in human and support the use of LAG-3 to boost the immunosurveillance of tumor cells in human.

EXAMPLE VI

CD8$^+$ T-cells Mediate the Primary Rejection

Figure 9A:
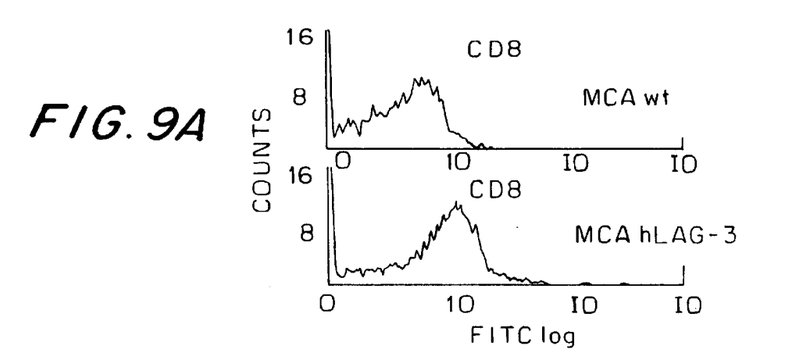
FIG. 9 illustrates rejection of hLAG-3+ tumor cells mediated by CD8+ lymphocytes.
Figure 9B:
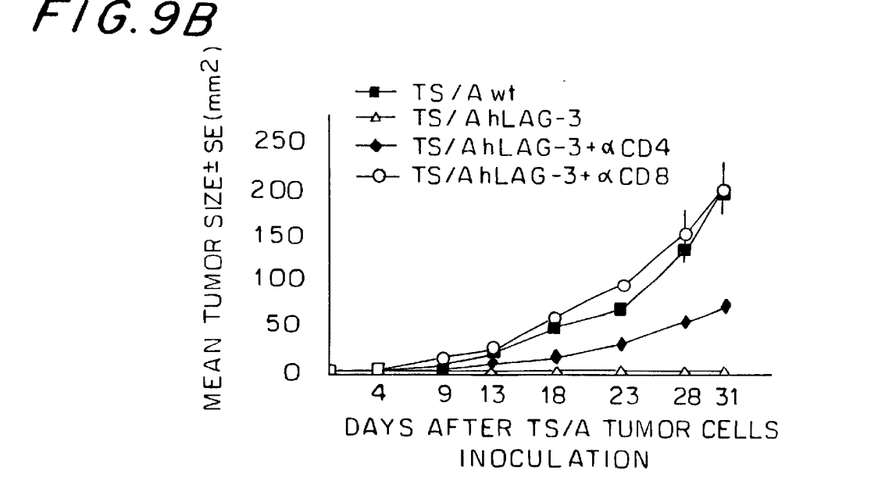

Rejection of hLAG-3 MCA 205 and TS/A transfectants was dependent on T-lymphocytes, as no rejection was observed in T-cell-deficient nu/nu mice. Following the injection of 5×MTD of these cells, 10 mm diameter tumors were excised at day 8 and both dissociated tumor cells and tumor infiltrating lymphocytes were analyzed by FACS. The wt tumors as well as the LAG-3 transfectants. initially CD80$^-$ and CD86$^-$, had remained negative for these markers following inoculation while LAG-3 was constantly detected on hLAG-3 tumors using the anti-LAG-3 17B4 mAb (data not shown). On day 8-explanted tumors, the percentage of CD8$^+$ cells was about 31% in hLAG-3 MCA 205 tumors versus 4% in wt MCA 205 tumors (FIG. 9*a*), whilst no difference was observed when analyzing the CD4$^+$, B or NK cell subsets. Similar results were obtained for TS/A tumors (data not shown). Finally, the respective contribution of CD4$^+$ and CD8$^+$ T-cells to the anti-tumor response was examined by depleting mice of these cell subsets. As shown in FIG. 9*b*, administration of the CD8-specific mAb at the time of hLAG-3/TS/A MTD inoculation abrogates the rejection of hLAG-3/TS/A tumor cells. Participation of CD4$^+$ helper T-cells is suggested by the partial effect observed with CD4-specific mAb (FIG. 9*b*).

EXAMPLE VII

Tumor-specific CTL Response is Enhanced by hLAG-3

Figure 9C:
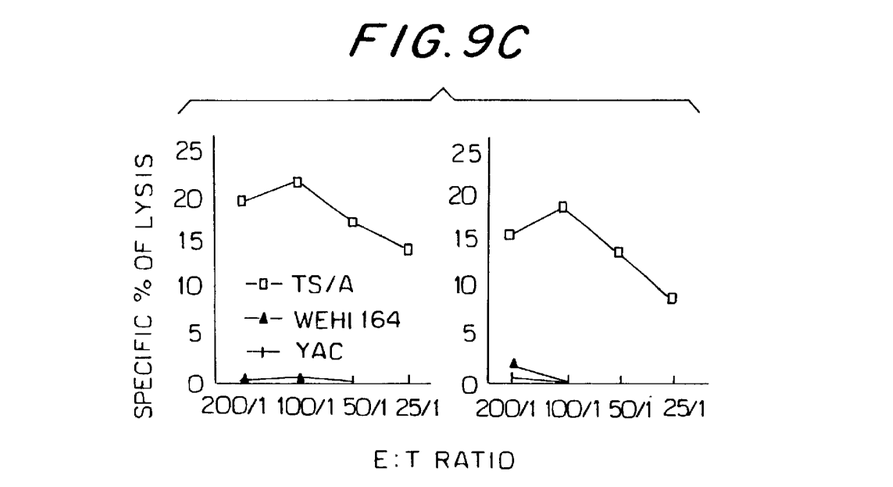

To further address the mechanism behind the anti-tumor activity of LAG-3, we evaluated its effect on the generation of cytotoxic T lymphocyte (CTL)– killing of the nonimmunogenic TS/A cells. Splenocytes were harvested from hLAG-3/TS/A tumor-implanted mice which were able to reject 5×MTD wt tumor cells in rechallenge experiments and were restimulated in vitro for 6 days with irradiated TS/A cells. CTL activity was detected in splenocytes of hLAG-3 tumor cell-implanted mice (FIG. 9*c*), while splenocytes from naive animals displayed no cytotoxic activity (data not shown). CTL activity appears to be selective for the nonimmunogenic TS/A cells since syngeneic WEHI sarcoma cells, as well as NK-sensitive YAC cells, were not lysed (FIG. 9*c*).

EXAMPLE VIII

Therapy of Established Tumors

Figure 10:
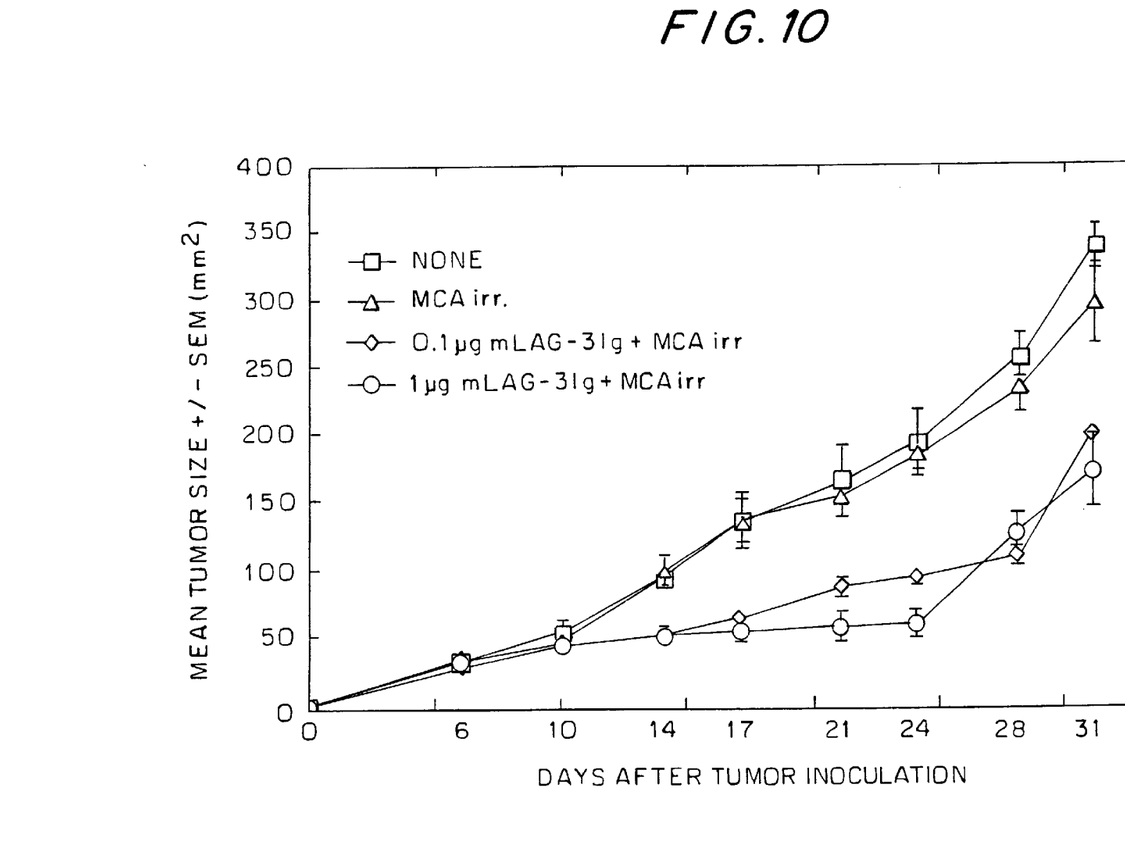
FIG. 10 represents the results (mean tumor size) of mice (20 C57BL/6 mice) grafted with a MTD of the syngeneic MCA 205 sarcoma cells receiving a single vaccine injection of LAG-3Ig. At day 6, 4 groups of 5 mice were formed and received a single s.c. vaccine injection (200 µl). The Ag is represented by irradiated (100 Gy) MCA 205 cells.

The inventors have shown that the control of tumor growth could be achieved by using a soluble LAG- molecule as a vaccine adjuvant. A single injection of a mixture of the antigen (irradiated tumor cells) plus the booster (mLAG-3lg, 1 μg or 0. 1 μg) was efficient (FIG. 10).

It is assumed that in vivo soluble LAG-3 molecules could signal the Langerhans cells (or any APC present at the vaccine site) via MHC class II molecules to prime efficiently CD8$^+$ T-cells.

REFERENCES

1. Triebel et a(, J. exp. Med., 1990, 171 :1393–1405
2. Baixeras et al., J. Exp. Med., 1992, 176: 327–337
3. Huard et al., Immunogenetics, 1994, 39: 213
4. Huard et al., Proc. Natl. Acad. Sci. U.S.A., 1997, 11:5744–5749
5. Huard et al., Eur. J. Immunol., 1994, 24: 3216–3221
6. Huard et al., Eur. J. Immunot., 1996, 26: 1180–1186
7. Miyazaki et al., Science, 1996, 272: 408
8. Angevin et al., Internal. J. of Cancer, 1997
9. Lurquin et al., Cell., 1992, 71: 1093
10. Takebe et al., J. Mol. and Cell. Biol., 1988, 8: 466
11. Cosgrove et al., Cell., 1991, 66: 1051
12. Restifo, N. P. & Wundertich, J. R. (1995) *Biology of Cellular Immune responses: Biological Therapy of Cancer*, eds. DeVita V., Heliman S & Rosenberg, S. (Lippincott, Philadelphia), pp 3–37.
13. Pardolt, D. M. (1995) *Annu. Rev. Immunol.* 13, 399–415.
14. Wade, W. F., Davoust, J., Salamero, J., Andre, P., Watts, T. H. & Cambier, J. C. (1993) *Immunology Today* 14. 539–542.
15. Koch, F., Stanzl, U., Jennewein, P., Janke, K., Heufler, C., Kampgen, E., Romani, N, & Schuler, G. (1996) *J. Exp. Med.* 184, 741–6.
16. Bruniquel, D., Borie. N. & Triebel, F. (1997) *Immunogenetics* 47, 96–98.
17. Huard, B., Prigent, P., Tournier, M., Bruniquel, D. & Triebel, F. (1995) *Eur. J. Immunol.* 25, 2718–2721.
18. McKinney, M. M. & Parkinson, A. (I1987) *J. Immunol. Methods* 96, 271–273.
19. H. Tighe, M. Corr, M. Roman & E. Raz, Immunology today, Feb. 19, 1998, N° 2, 89–96.

What is claimed is:

1. A pharmaceutical composition comprising an effective amount of an antigen able to induce an antigen-specific immune response together with an effective amount of a MHC class II ligand able to boost said antigen-specific immune response, wherein said MHC class II ligand is selected from the group consisting of hLAG-3 and a soluble fragment of hLAG-3, and is present as an adjuvant agent.

2. A pharmaceutical composition comprising an effective amount of an antigen able to induce an antigen-specific T-cell mediated immune response together with an effective amount of a MHC class II ligand able to boost said antigen-specific T-cell mediated immune response, wherein said MHC class II ligand is selected from the group consisting of hLAG-3 and human soluble LAG-3 and is present as an adjuvant agent.

3. A pharmaceutical composition according to claim 2, wherein said MHC class II ligand is hLAG-3.

4. A pharmaceutical according to claim 2, wherein said MHC class II ligand is human soluble LAG-3.

5. A pharmaceutical composition according to claim 2 as a vaccine.

6. The pharmaceutical composition according to claim 1, wherein said MHC class II ligand is hLAG-3.

7. The pharmaceutical composition according to claim 1 wherein said MHC class II ligand is a soluble hLAG-3 fragment.

8. The pharmaceutical composition according to claim 7, wherein said soluble LAG-3 fragment is selected from the group consisting of D1–D2 and D1–D4 fragments of LAG-3.

9. A method for preventing or treating a pathological condition involving an antigen specific immune response, comprising administering the pharmaceutical composition of claim 1 to a subject in need thereof.

10. A method for treating conditions requiring induction of $CD8^+$ T-cell immunity, comprising administering a therapeutic vaccine in which LAG-3 is an adjuvant.

11. A method for preventing or treating a pathological condition involving an antigen specific T-cell mediated immune response, comprising administering the pharmaceutical composition of claim 2 to a subject in need thereof.

12. The method according to claim 11, wherein the pathological condition involving an antigen specific T-cell mediated immune response is selected from the group consisting of viral infectious diseases, parasitic infectious diseases, bacterial infectious diseases, and cancer.

13. The method according to claim 11 wherein said MHC class II ligand of the administered pharmaceutical composition is soluble LAG-3.

14. The method according to claim 13, wherein the pathological condition involving an antigen specific T-cell mediated immune response is selected from the group consisting of viral infectious diseases, parasitic infectious diseases, bacterial infectious diseases, and cancer.

15. The method according to claim 9, wherein the pathological condition involving an antigen specific immune response is selected from the group consisting of viral infectious diseases, parasitic infectious diseases, bacterial infectious diseases, and cancer.

16. A pharmaceutical composition for the treatment or prevention of pathological conditions involving an antigen specific T-cell mediated immune response, comprising an effective amount of a MHC class II ligand able to boost said antigen specific T-cell mediated immune response, wherein the MHC class II ligand is LAG-3, and a pharmaceutically acceptable vehicle.

17. A pharmaceutical composition comprising an effective amount of an antigen able to induce an antigen-specific immune response together with an effective amount of an MHC class II ligand, wherein the MHC class II ligand is a soluble 52 kD polypeptide of hLAG-3 comprising extracellular domains D1, D2 and D3, or a mutant form of a soluble fragment of hLAG-3 comprising the extracellular domains D1 and D2, said mutant defined by one or more amino acid substitutions selected from the group consisting of Arg at residue position 73 substituted with Glu,
Arg at residue position 75 substituted with Ala,
Arg at residue position 75 substituted with Glu,
Arg at residue position 76 substituted with Glu,
Asp at residue position 30 substituted with Ala,
His at residue position 56 substituted with Ala,
Arg at residue position 88 substituted with Ala, and
Arg at residue position 103 substituted with Ala.

18. The pharmaceutical composition according to claim 17 as a vaccine.

19. The pharmaceutical composition according to claim 17 wherein said antigen-specific immune response is an antigen-specific T-cell mediated immune response.

20. A method for preventing or treating a pathological condition involving an antigen specific immune response, comprising administering the pharmaceutical composition of claim 17 to a subject in need thereof.

21. The method according to claim 20, wherein the pathological condition involving an antigen-specific immune response is selected from the group consisting of viral infectious diseases, parasitic infectious diseases, bacterial infectious diseases, and cancer.

22. A method according to claim 20, wherein said antigen-specific immune response is an antigen-specific T-cell mediated immune response.

* * * * *